United States Patent
Monty et al.

(10) Patent No.: US 9,450,369 B2
(45) Date of Patent: Sep. 20, 2016

(54) SYSTEMS AND METHODS FOR SUPPLYING POWER TO AND COOLING DENTAL LASER SYSTEMS

(71) Applicant: Convergent Dental, Inc., Natick, MA (US)

(72) Inventors: Nathan P. Monty, Shrewsbury, MA (US); William H. Groves, Jr., Arlington, MA (US)

(73) Assignee: Convergent Dental, Inc., Natick, MA (US)

(*) Notice: Subject to any disclaimer, the term of this patent is extended or adjusted under 35 U.S.C. 154(b) by 0 days.

(21) Appl. No.: 14/952,396

(22) Filed: Nov. 25, 2015

(65) Prior Publication Data

US 2016/0149369 A1 May 26, 2016

Related U.S. Application Data (60) Provisional application No. 62/084,786, filed on Nov. 26, 2014.

(51) Int. Cl.
*H01S 3/00* (2006.01)
*H01S 3/102* (2006.01)
(Continued)

(52) U.S. Cl.
CPC .............. *H01S 3/1024* (2013.01); *H01S 3/041* (2013.01); *H01S 3/0407* (2013.01); *H01S 3/0975* (2013.01); *H01S 3/09702* (2013.01); *H01S 3/10046* (2013.01); *H01S 3/2232* (2013.01); *A61C 1/0046* (2013.01); *H01S 3/0315* (2013.01); *H01S 3/0971* (2013.01); *H01S 3/104* (2013.01)

(58) Field of Classification Search
CPC .............. H01S 3/1024; H01S 3/10046; H01S 3/0975; H01S 3/2232; H01S 3/041; H01S 3/0407
USPC ..................... 372/38.04, 35, 4, 38.07, 55, 82
See application file for complete search history.

(56) References Cited

U.S. PATENT DOCUMENTS 3,491,309 A 1/1970 Hill
3,605,038 A 9/1971 Byrne et al.
(Continued)

FOREIGN PATENT DOCUMENTS

CN 200987034 Y 12/2007
CN 102496839 A 6/2012
(Continued)

OTHER PUBLICATIONS

International Search Report and Written Opinion for PCT/US2015/062766, mailed Mar. 14, 2016 (13 pages).
(Continued)

*Primary Examiner* — Kinam Park
(74) *Attorney, Agent, or Firm* — Goodwin Procter LLP (57) ABSTRACT

A dental laser system is configured to provide high peak laser power, low duty cycle laser pulses, yielding a low average laser power and thus a reduced need for cooling. The laser power system may be configured to provide the electrical power required to produce the low average laser power and not the high peak laser power, and may include a capacitor bank section configured to provide the electrical power needed to produce the high peak power laser pulses. The cooling system may be configured to provide laser cooling for the low average power level and thus may not require a refrigeration unit.

47 Claims, 9 Drawing Sheets

(51) Int. Cl.
| | |
|---|---|
| *H01S 3/223* | (2006.01) |
| *H01S 3/04* | (2006.01) |
| *H01S 3/041* | (2006.01) |
| *H01S 3/10* | (2006.01) |
| *H01S 3/0975* | (2006.01) |
| *H01S 3/097* | (2006.01) |
| *A61C 1/00* | (2006.01) |
| *H01S 3/0971* | (2006.01) |
| *H01S 3/104* | (2006.01) |
| *H01S 3/03* | (2006.01) |

(56) References Cited

U.S. PATENT DOCUMENTS

| | | | |
|---|---|---|---|
| 4,575,853 | A | 3/1986 | Jako |
| 4,679,202 | A | 7/1987 | Maloney et al. |
| 4,785,456 | A | 11/1988 | Kaplan |
| 5,283,797 | A | 2/1994 | Mefferd |
| 5,401,171 | A | 3/1995 | Paghdiwala |
| 6,157,661 | A | 12/2000 | Walker et al. |
| 6,693,944 | B1 * | 2/2004 | Hug ............ H01S 3/031 372/55 |
| 2003/0128554 | A1 * | 7/2003 | Crewson ........ H01F 30/06 363/16 |
| 2003/0198264 | A1 | 10/2003 | Vetrovec et al. |
| 2008/0000613 | A1 | 1/2008 | Harpole |
| 2011/0085576 | A1 * | 4/2011 | Crawford ...... H05B 33/0818 372/38.07 |
| 2011/0243177 | A1 | 10/2011 | Nishio et al. |
| 2013/0253411 | A1 | 9/2013 | Rubinchik et al. |

FOREIGN PATENT DOCUMENTS

| | | |
|---|---|---|
| EP | 0776073 A1 | 5/1997 |
| JP | S60170279 A | 9/1985 |
| WO | WO-2007144645 A1 | 12/2007 |

OTHER PUBLICATIONS

Cooler Radiators for CO2 Laser Cooling, downloaded from: <http://www.lightobject.com/12inch-300mm-Water-Evaporator-Cooler-Radiators-for-CO2-Laser-Cooling-P713.aspx>, on Aug. 7, 2014, 2 pages.

Laser FocusWorld, Ten rules to guide liquid-cooling decisions, downloaded from: http://www.laserfocusworld.com/articles/print/volume-38/issue-7/features/ten-rules-to-guide-liquid-cooling-decisions.html, on Aug. 7, 2014, 11 pages.

Lytron, "Liquid Cooling a Laser for System Optimization," downloaded from: http://www.lytron.com/Tools-and-Technical-Reference/Application-Notes/Liquid-Cooling-a-Laser-for-System-Optimization, on Aug. 5, 2014, 3 pages.

Online Catalog, "Stainless Steel Heat Exchangers—4000 Series," downloaded from: www.Lytron.com, (2016), 6 pages.

Sam's Laser FAQ, "Carbon Dioxide Lasers," downloaded from: http://www.repairfaq.org/sam/laserco2.htm, on Aug. 7, 2014, 58 pages.

Sam's Laser FAQ, "Home-Built Carbon Dioxide (CO2) Laser," downloaded from: http://www.repairfaq.org/sam/laserco2.htm, on Aug. 7, 2014, 81 pages.

Snapshot, "Surgical Properties and Applications of Sealed Off CO2 Lasers," (Book) Biomedical Optical Instrumentation and Laser-Assisted Biotechnology, (1995), Chapter XXII, p. 235.

Thermatron, "High Reliability, Compact Liquid-to-Air Heat Exchangers," Website: http://www.thermatroneng.com. (1994), 4 pages.

Patentability Search, "Medical Laser Systems," Greyb Services Pte, Ltd., Aug. 8, 2014, 50 pages.

* cited by examiner

| Parameter | Min | Nominal | Max | Unit |
|---|---|---|---|---|
| Peak Fluence for Laser-Based Dental Treatment | 1 | 10 | 500 | J/cm2 |
| Peak Power Output of the Laser | 10 | 400 | 1000 | W |
| Peak Power Input of the Laser | 300 | 12000 | 30000 | W |
| Average Power Output of the Laser | 0.5 | 20 | 50 | W |
| Average Power Input of the Laser | 15 | 600 | 1500 | W |
| Pulse Energy | 1 | 40 | 100 | mJ |
| Pulse Cycle (ON and OFF duration of pulse) | 10 | 100 | 5000 | μsec |
| Pulse Width (ON duration of pulse) | 1 | 50 | 500 | μsec |
| Duty Cycle | 1 | 5 | 50 | % |
| Peak Power Per Pulse | 10 | 400 | 1000 | W |
| Average Power Per Pulse | 0.05 | 0.25 | 2.5 | W |
| Input Voltage of Power Supply | 100 | 120 | 600 | V |
| Input Current of Power Supply | 2 | 8 | 30 | A |
| DC Output Voltage of Power Supply | 24 | 48 | 144 | V |
| DC Output Current of Power Supply (Current Delivered to Capacitor Bank) | 1 | 10 | 100 | A |
| Output Voltage of Capacitor Bank | 24 | 48 | 144 | V |
| Output Voltage of Individual Capacitors in Capacitor Bank | 24 | 48 | 144 | V |
| Capacitance of Individual Capacitors in Capacitor Bank | 1000 | 68000 | 150000 | μF |
| Number of Capacitors in Capacitor Bank | 1 | 4 | 100 | |
| Output Current of Capacitor Bank | 10 | 100 | 1000 | A |
| Change in Laser Temperature from Ambient to Steady State | 1 | 10 | 40 | °C |
| Rate of Change of Laser Temperature | 0.001 | 0.2 | 25 | °C/min |

SYSTEMS AND METHODS FOR SUPPLYING POWER TO AND COOLING DENTAL LASER SYSTEMS

CROSS-REFERENCE TO RELATED APPLICATIONS

This application claims the benefit of priority to U.S. Provisional Patent Application No. 62/084,786, entitled "Systems and Methods for Supplying Power to and Cooling Dental Laser Systems," filed Nov. 26, 2014, the disclosure of which is incorporated herein by reference in its entirety.

FIELD OF THE INVENTION

The present disclosure relates generally to a gas discharge laser and, in particular, to a pulsed laser system and the associated power supply and cooling systems.

BACKGROUND

Lasers are useful in a multitude of hard and soft tissue dental procedures, including: removing decay, cutting, drilling or shaping hard tissue, and removing or cutting soft tissue. A tooth has three layers: the outermost layer is the enamel which is the hardest and forms a protective layer for the rest of the tooth. The middle and bulk of the tooth includes dentin, and the innermost layer includes pulp. The enamel and dentin are similar in composition and are roughly at least 70% mineral by weight, which includes carbonated hydroxyapatite, while the pulp contains vessels and nerves. Lasers at a wavelength in a range of 9.3 to 9.6 µm are well absorbed by the hydroxyapatite that is a significant component of tooth and bone, making such lasers efficient in the removal of hard tissue. The use of $CO_2$ laser applications in dentistry has increased recently, e.g., with $CO_2$ laser wavelength bands ranging between 9.3 and 10.6 µm. At wavelengths in the range 9.6 and 10.6 µm, phosphate absorption generally drops significantly, and thus dental lasers for the removal of hard tissue may be operated in the 9.3 to 9.6 µm wavelength range.

Lasers have been found to be useful in the removal of dental material without needing local anesthetic that is required when a similar procedure is performed with a drill. Further, lasers do not make the noises and vibrations that are associated with dental drills. At least for these reasons, it has been the hope of many in the dental industry that lasers may replace the drill and remove or at least reduce much of the discomfort, anxiety and fear from dental treatment.

In general, the optical power output of a laser beam can be described as the continuous power output of a continuous wave (CW) laser, or the average power output of a pulsed or modulated laser. The input laser power is measured in watts (sometimes referred to herein as "electrical power"), and the output laser power that irradiates a surface area (described e.g., in $cm^2$) may be measured in watts/$cm^2$ (sometimes referred to herein as "laser power," or irradiance). The average power of a pulsed laser is the pulse energy multiplied by the laser repetition rate, where the pulse energy is in joules and the repetition rate is in hertz, or pulses per second. A maximum average laser power level for a pulsed laser can be calculated from pulse energy at the maximum laser repetition rate (pulses per second). The peak power of a pulsed laser can be described as the peak pulse energy divided by the pulse ON duration. For a given repetition rate, the pulse duty cycle is the percentage of the pulse cycle time/period that the ON duration of a pulse occupies.

Laser-mediated ablation of hard materials such as hydroxyapatite may require high peak pulse powers and short pulse durations (ON durations). The peak laser power required, in general, is a function of the laser power required to cleanly ablate hard dental tissue. The high peak laser power requirement often results in the use of an electrical power supply that may continuously provide the electrical power required for generating the laser pulse. For example, if for a particular application, the required laser power per pulse is 4 KW, a power supply capable of providing a continuous laser power output around 4 KW is traditionally selected. Such high-powered laser systems may also require cooling with a circulated coolant, generally using a refrigerated chiller, to remove heat from the coolant. The refrigerated chiller can add considerable volume and expense.

Various known techniques for supplying power to and/or cooling of laser-based dental treatment systems generally suffer from a number of disadvantages. For example, some known systems use a laser with a power rating that is significantly higher than that required for dental treatment applications, requiring an electrical power supply capable of providing the higher electrical power to such a laser. Some systems use a power source rated for continuous delivery of the power that is required to produce the peak laser output power. Such power source can be bulky, expensive, and may require cooling in addition to the laser-beam generator (also called laser). Furthermore, conventional techniques generally employ refrigeration systems in order to cool the heat produced by a laser with a high laser power rating.

SUMMARY

This disclosure describes techniques for increasing laser power efficiency, increasing laser cooling efficiency, and improving laser thermal configuration for effective laser-based dentistry. In particular, in various embodiments, a dental laser capable of cutting both hard tissue and soft tissue, which may include a $CO_2$ laser with a high peak laser power output, is operated such that the average output laser power is significantly less (e.g., up to 50% or less) than the peak output laser power required for the selected dental treatment. Such a laser may produce less heat and may require less cooling than a laser operated to produce a greater average laser power output.

Moreover, the laser may be operated using an electrical power supply that is not rated for the power required to produce the high peak laser power. Instead, the power supply may be rated and operated at a power required to produce the significantly lower average laser power. A capacitor bank may be used to store energy and release the stored energy during ON duration of laser pulses, thereby providing sufficient power to the laser to produce pulses having the high peak power. This can reduce the amount of heat dissipated by the overall system even further.

The overall system including the laser and the power supply subsystem may therefore be configured to use a simpler cooling apparatus that does not require a refrigeration system. Such a dental laser system may deliver sufficient high peak laser power to ablate hard dental tissue. while operating at a low average laser power, and without needing refrigerated cooling or a high-capacity electrical power supply. A fan-cooled, radiator-based coolant system may be configured for the lower laser average power instead of for the peak power, so that a conventional refrigerated chiller is not needed.

To this end, one aspect of the present disclosure includes a laser system featuring a laser for generating a pulsed laser beam and a controller configured to trigger the laser at a specified peak output laser power and at an average output laser power of less than approximately 50% of the specified peak output laser power. The system may include a power source supplying input laser power to the laser and rated at less than input laser power corresponding to the specified peak output laser power. The system may also include a capacitor bank having at least one capacitor and configured for charging the capacitors from the power source and for delivering to the laser at least a portion of an input laser power corresponding to the specified peak output laser power during an ON duration of a pulse.

In various embodiments a wavelength of the laser is in a range from 8 μm up to 12 μm. The laser may be rated to have a maximum average output laser power level less than approximately 50% of the specified peak output laser power. In some cases, the specified peak output laser power is within a range from 10 W up to 1,000 W. The controller may be adapted to adjust the average output laser power: (i) within a range from 0.5 W up to 50 W; (ii) within a range from 0.5 W to 500 W; or (iii) to a level of at least 50 W. The controller may be adapted to limit the average output laser power up to 10% (or in some cases, up to 5%) of the specified peak output laser power. In certain instances, the controller is adapted to adjust a duration of the pulse of the pulsed laser beam within a range from 10 μs up to 5,000 μs, and/or to adjust a duty cycle of the pulse within a range from 1% up to 50%.

In various embodiments, an output voltage of the capacitor bank is within a range from 24 V up to 144 V, and a peak current of the capacitor bank is within a range from 10 A up to 1,000 A. The number of capacitors in the capacitor bank may be in a range from 1 up to 100, and a capacitance of each capacitor may be within a range from 1,000 μF up to 150,000 μF. In some instances, the controller is adapted to adjust the peak output laser power to a level sufficient to ablate dental enamel. In some instances, the controller is adapted to operate the laser at an average output laser power less than a rated maximum average output laser power level of the laser. The laser may feature a waveguide in at least one optical resonator axis. In some cases, the laser includes a gas discharge laser (e.g., a $CO_2$ laser).

In various embodiments, the laser may further include a non-refrigerant-based cooling system for controlling an operating temperature of at least the laser. The non-refrigerant-based cooling system may include: at least one laser coolant path in thermally conductive communication with the laser, a coolant reservoir for containing a coolant (e.g., water), a pump for circulating the coolant; and a radiator having at least one heat-conducting pathway therethrough. In some cases, the cooling system may also have: a level sensor for measuring a level of the coolant in the coolant reservoir; a temperature sensor for measuring temperature of the coolant; a flow sensor for measuring a flow of the coolant; and a fan directing air flow to the heat-conducting pathway. In certain implementations, the controller may be adapted to suspend operation of the laser based on an output from the level sensor, the temperature sensor, and/or the flow sensor. The controller may be adapted, based on an output from the temperature sensor, to either: (i) adjust the pump to adjust a flow of the coolant; and/or (ii) operate the fan. For example, the controller may adjust the pump and/or the fan so as to limit a temperature of the coolant to at most 30° C.

In general, in another aspect, embodiments of the disclosure feature a method of operating a laser, which may include the step of generating a pulsed laser beam, generation of laser pulses comprising configuring the laser to trigger at a specified peak output laser power and at an average output laser power of less than approximately 50% of the specified peak output laser power. The method may also include charging at least one capacitor in a capacitor bank using a power source rated at less than an input laser power corresponding to the specified peak output laser power. The method may also include delivering to the laser from the capacitor bank at least a portion of the input laser power corresponding to the specified peak output laser power during an ON duration of a laser pulse.

In various embodiments, a wavelength of the laser is in a range from 8 μm up to 12 μm. The laser may be rated to have a maximum average output laser power level less than approximately 50% of the specified peak output laser power. The specified peak output laser power may be within a range from 10 W to 1,000 W. In some instances, the configuring step may include adjusting the average output laser power: (i) within a range from 0.5 W up to 50 W (or in some cases, up to 500 W) or (ii) to a level of at least 50 W. The configuring step may also include limiting the average output laser power up to 10% (or in some cases, up to 5%) of the specified peak output laser power. In some cases, the configuring step further includes adjusting a duration of the pulse of the pulsed laser beam within a range from 10 μs up to 5,000 μs, and/or adjusting a duty cycle of the pulse of the pulsed laser beam within a range from 1% up to 50%.

In various embodiments, the delivering step may include delivering an output voltage within a range from 24 V up to 144 V, and delivering a peak output current within a range from 10 A up to 1,000 A. The number of capacitors in the capacitor bank may be in a range from 1 up to 100, and the capacitance of each capacitor may be within a range from 1,000 μF up to 150,000 μF. In some instances, the configuring step includes adjusting the peak output laser power to a level sufficient to ablate dental enamel. The configuring step may also include configuring the laser to operate at an average output laser power less than a rated maximum average output laser power level of the laser.

In various embodiments, the method may include controlling an operating temperature of at least the laser using a non-refrigerant-based cooling system. In some instances, the method also includes obtaining an output from a level sensor, a temperature sensor, and/or a flow sensor of the non-refrigerant-based cooling system, and suspending operation of the laser based on the reading. In other instances, the method includes obtaining an output from a temperature sensor of the non-refrigerant-based cooling system and (i) adjusting a flow of coolant and/or (ii) operating a fan, based on the reading. In such instances, adjusting the flow and/or operating the fan may limit a temperature of the coolant to at most 30° C.

In general, in another aspect, embodiments of the disclosure feature a high peak power, low average power laser system. The laser system can include a laser operating at a wavelength in the range from 8 to 12 μm, at least one controller configured to operate the laser at an average laser power lower than the maximum average laser power, and a cooling system configured to remove heat produced by the laser. The laser may have a waveguide in at least one optical resonator axis and be configured to provide laser pulses having a high peak laser power. The high peak laser power may be sufficient to ablate dental enamel. The maximum average laser power level may be less than approximately 50% of the high peak laser power.

In various embodiments, the laser system may also include an electrical power system configured to provide electrical power to operate the laser at the lower average laser power. In some cases, the electrical power system has an AC to DC power supply and at least one capacitor bank in electrical communication with the AC to DC power supply. In general, the electrical power corresponding to the peak/average output laser power is the electrical power required by the laser to produce the peak/average output laser power and may also include electrical power that is slightly greater or slightly less, e.g., with a tolerance of 1%, 2%, 5%, 10%, 20%, etc., than the required electrical power. The capacitor bank may be configured to provide the peak electrical power required to provide the laser pulses. In some cases, the controller is configured to operate the pulsing of the laser at a low duty cycle. The high peak laser power may be greater than 50 W, and the lower average laser power may be in the range of approximately 1 to 30 W. In some cases, the lower average laser power is less than or equal to approximately 10% (or in some cases, less than or equal to approximately 5%) of the high peak laser power. The laser pulses may have a pulse duration in the range of approximately 0.001 ms to 10 ms, and/or the low duty cycle may be less than or equal to approximately 10%. In some cases, the laser is a gas discharge laser (e.g., a $CO_2$ laser).

In various embodiments, the cooling system may include any or all of the following: at least one laser coolant path in thermally conductive communication with the laser; a coolant reservoir containing a coolant (e.g., water) at ambient temperature; a level sensor for measuring the level of coolant in the coolant reservoir; a temperature sensor for measuring the temperature of the coolant; a pump for circulating the coolant; a flow sensor for measuring the flow of the coolant; a radiator having at least one heat-conducting pathway therethrough; a fan providing heat removal from the heat-conducting pathway; and tubing for providing a flow path for the coolant to and from the laser coolant path, the coolant reservoir, the pump, the flow sensor, and/or the radiator. The cooling system may not permit a coolant temperature of more than 30° C. during operation, either (i) at less than or equal to 50% on-time or duty cycle and/or (ii) during fully continuous operation. The laser may, in some cases be configured for dental treatment (e.g., dental surgery).

In general, in another aspect, embodiments of the disclosure feature a high peak power, low average power laser system that includes a laser operating at a wavelength in the range of 8 to 12 µm, at least one controller configured to operate the laser at a low duty cycle and a lower average power, and an electrical power supply configured to provide electrical power to operate the laser at the lower average laser power. The system may also include a cooling system configured to remove heat produced by the laser at the lower average laser power. The laser may have a waveguide in at least one optical resonator axis and be configured to provide laser pulses having a high peak laser power having sufficient irradiance to ablate dental enamel. The laser may have a maximum average laser power level that is less than approximately 50% of the high peak laser power. In some cases, the electrical power supply may have an AC to DC power supply and at least one capacitor bank in electrical communication with the AC to DC power supply. The capacitor bank may be configured to provide peak electrical power required to provide the laser pulses. The cooling system may include any or all of: at least one laser coolant path in thermally conductive communication with the laser; a coolant reservoir containing a coolant (e.g., water) at ambient temperature; a level sensor for measuring the level of coolant in the coolant reservoir; a temperature sensor for measuring the temperature of the coolant; a pump for circulating the coolant; a flow sensor for measuring the flow of the coolant; a radiator having at least one heat-conducting pathway therethrough; a fan providing heat removal from the heat-conducting pathway; and tubing for providing a flow path for the coolant to and from the laser coolant path, the coolant reservoir, the pump, the flow sensor, and/or the radiator.

In various embodiments, the high peak laser power may be greater than 50 W and the lower average laser power may be in the range of approximately 1-30 W. In some instances, the lower average power is less than or equal to approximately 10% (or in some cases, less than or equal to approximately 5%) of the high peak laser power. The laser pulses may have a pulse duration in the range of approximately 0.001 ms to 10 ms. In some cases, the low duty cycle is less than or equal to approximately 10%. The laser may be a gas discharge laser (e.g., a $CO_2$ laser). The cooling system may not permit a coolant temperature of more than 30° C. during operation, either (i) at less than or equal to 50% on-time or duty cycle and/or (ii) during fully continuous operation. The laser may, in some cases be configured for dental treatment (e.g., dental surgery).

BRIEF DESCRIPTION OF THE FIGURES

Various aspects of this disclosure will become more apparent in view of the attached drawings and accompanying detailed description. The embodiments depicted therein are provided by way of example, not by way of limitation, wherein like reference numerals generally refer to the same or similar elements. In different drawings, the same or similar elements may be referenced using different reference numerals. The drawings are not necessarily to scale, emphasis instead being placed upon illustrating aspects of the invention. In the drawings.

DETAILED DESCRIPTION

Figure 1:
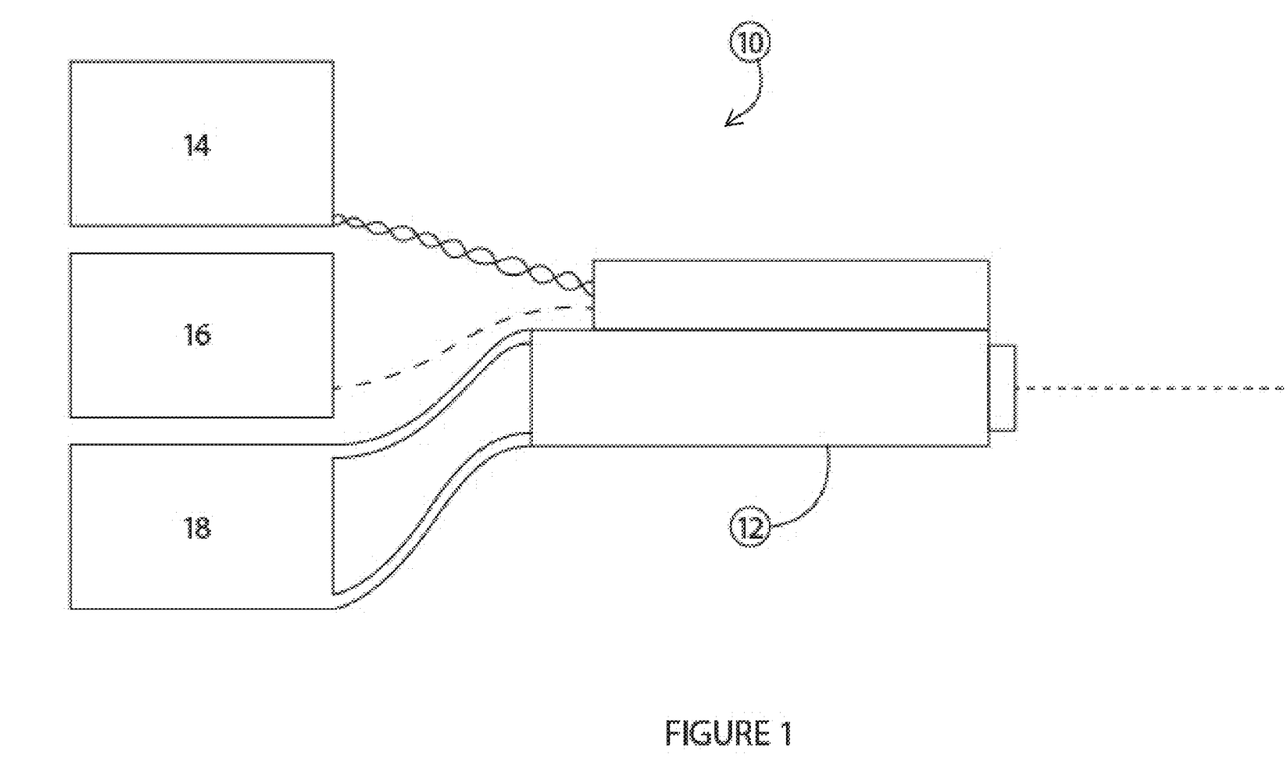
FIG. 1 is a schematic block diagram of an exemplary dental laser system, according to various embodiments.

With reference to FIG. 1, various embodiments described herein include a high peak output power, low average output power laser system 10 that includes a laser 12, an electrical power system 14, at least one controller 16, and a cooling system 18. For use in dental treatment, the system 10 may be configured to use a $CO_2$ laser to emit laser pulses having a high peak laser power. For example, the $CO_2$ laser may be configured with an increased gas pressure to increase the high peak output laser power. Systems for increasing the peak power of a gas discharge laser are described in U.S. Pat. No. 8,251,984, which is incorporated herein by reference in its entirety.

Figure 2:
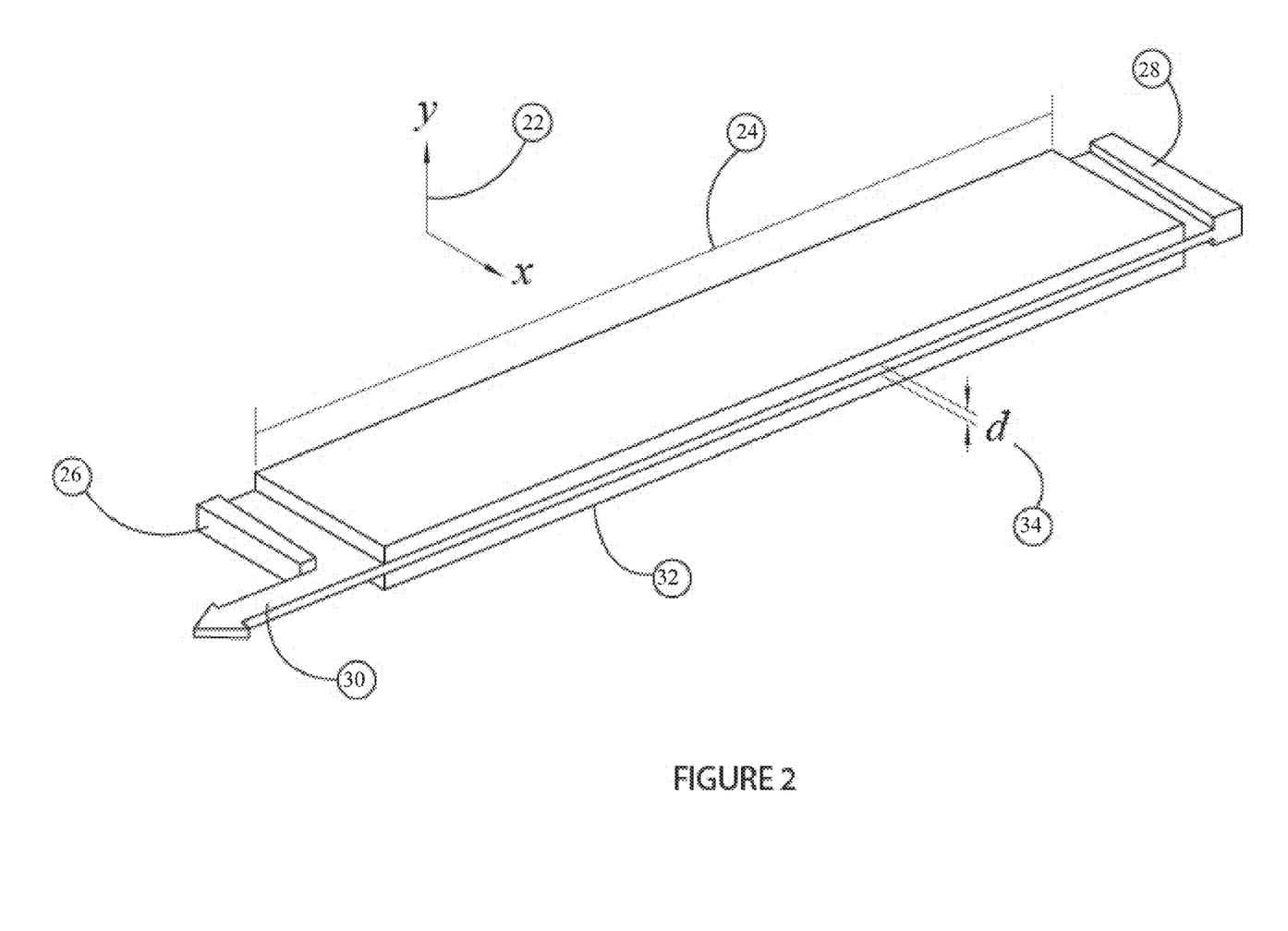
FIG. 2 is a schematic diagram of a resonator portion of a $CO_2$ laser, according to various embodiments.

FIG. 2 shows a resonator of a $CO_2$ laser 30 that may be featured in various embodiments described herein. $CO_2$ lasers having a wavelength in the range of 8 to 12 μm can ablate both hard and soft tissue and may be used for dental treatment. FIG. 2 shows optical resonator axes diagramed in an X-Y format 22. Curvature of a front mirror 26 optically communicates with curvature of a rear mirror 28. The front mirror and the rear mirror are separated by a length of at least two electrodes 24 to form an optical resonator. The curvatures of the front mirror 26 and the rear mirror 28 can be chosen to control the optical energy in the X, or the Y, or in both the X and Y axes. Direct current and various frequencies of electrical energy can be used to form a plasma discharge between the two electrodes 32 that are separated by a gap "d" shown at 34. The curvature of the front mirror 26 in combination with the curvature of the rear mirror 28 can form a stable resonator or an unstable resonator. In some instances, the curvature of the front mirror 26 can couple into the gap 34 to form a waveguide in at least one optical resonator axis. The waveguide can exist in either the X or Y axis. In some instances, the gap 34 used to form an optical resonator axis may be 5 mm or less, and may facilitate close electrode spacing for more efficient cooling of the laser discharge between the electrodes.

Figure 3:
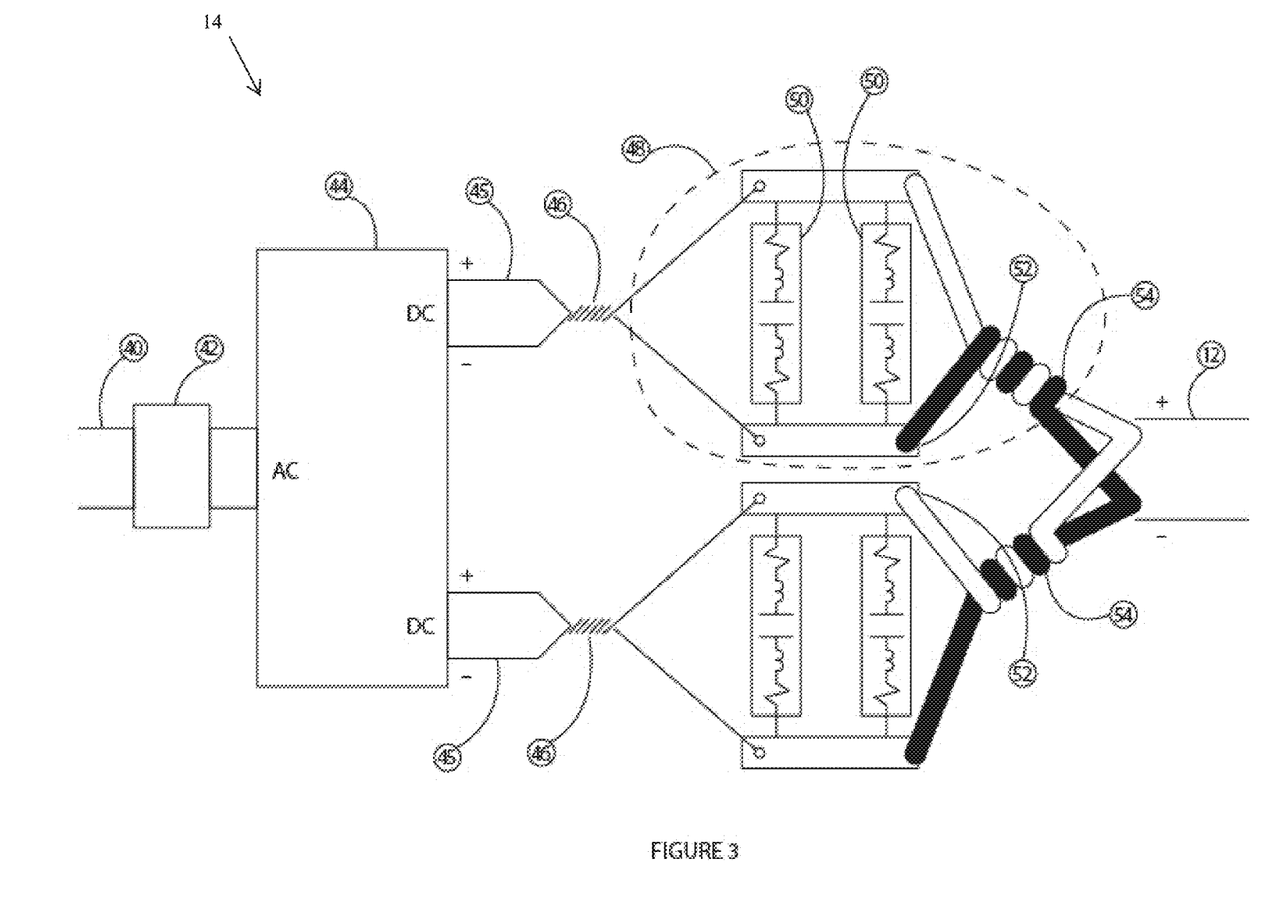
FIG. 3 is a schematic block diagram of an electrical power system for the laser, according to various embodiments.

FIG. 3 shows an example electrical power system 14, which is configured to provide electrical power to the laser 12. In order to produce laser pulses having high peak laser power, the laser must be provided with sufficient electrical power. In the embodiment shown in FIG. 3, AC mains 40 are conditioned by an AC filter 42 to remove line noise, and the filtered AC signal is fed into an AC to DC power supply 44 (e.g., a medical grade AC to DC switch-mode power supply with power factor correction). In various embodiments, the input voltage supplied to the AC mains 40 may be, e.g., 110V, 120V, 230V, 240V, 480V, 600V, etc. The input current at the AC mains 40 may be, e.g., 2 A, 4 A, 6 A, 10 A, 12 A, 14 A, 16 A, 18 A, 20 A, 22 A, 24 A, 26 A, 28 A, 30 A, 100 A, 1000 A, etc.

The AC to DC power supply 44 may have one or more power supply outputs 45. The power supply outputs 45 may provide electrical power at a required DC voltage (i.e., the effort at which electrical power is provided to the laser) and a low average DC current. For example, the power supply output 45 may be two pairs of floating (ungrounded) terminals that provide a required voltage of 48V, having an average current of 10 A. The required voltage of 48V may be suitable to generate laser pulses having a high peak output laser power that is a maximum peak output laser power according to a configuration of the laser. In various embodiments, the power supply output 45 may provide, e.g., 24V, 48V, 144V, etc. The power supply output 45 may provide an output current of, e.g., 1 A, 5 A, 10 A, 20 A, 30 A, 40 A, 50 A, 60 A, 70 A, 80 A, 90 A, 100 A, etc.

In various embodiments, the required voltage may be varied in order to control the high peak power of the laser pulses. For example, a voltage less than that required to produce laser pulses with the maximum peak output laser power can produce laser pulses having a peak output laser power that is less than the maximum peak output laser power. The power supply outputs 45 may be connected using twisted pair leads 46 to one or more capacitor banks 48. Each of the capacitor banks 48 may include one or more capacitors 50. In various embodiments, each capacitor bank may include 1, 2, 4, 6, 8, 10, 20, 40, 60, 80, 100, etc., individual capacitors. The twisted pair leads 46 can lower the radiated electromagnetic energy (EMC) of the electrical power system 14.

The electrical power from the AC to DC power supply 44 may charge the capacitors 50 up to a certain specified voltage. The capacitance of each capacitor in the capacitor bank may be, e.g., 1000 μF, 2000 μF, 5000 μF, 10,000 μF, 20,000 μF, 40,000 μF, 60,000 μF, 100,000 μF, 150,000 μF, etc. The output voltage of the capacitor bank (or in some cases, of each capacitor in the capacitor bank) may be, e.g., 24V, 48V, 144V, etc. The output current of the capacitor bank may be, e.g., 10 A, 20 A, 50 A, 100 A, 200 A, 300 A, 400 A, 500 A, 600 A, 700 A, 800 A, 900 A, 1000 A, etc. In some instances, the capacitors 50 may have low voltage and high capacitance. Within the capacitor banks 48, the capacitors 50 may be arranged in parallel in order to optimize the inherent series impedances of the capacitors 50. The capacitor banks 48 can thus deliver high discharge current as required for high peak laser power pulses, while maintaining and keeping substantially constant the required voltage.

In various embodiments, the capacitor banks 48 are in electrical communication with the laser 12 through one or more low impedance bus bars 52 and one or more low impedance twisted pair leads 54. Thus, the capacitors in the banks 48 can deliver a high electrical current at the required voltage, and thus the power required to generate the laser pulses at the specified peak laser power and average laser power with minimal loss of energy, while meeting EMC requirements. In some embodiments, the AC to DC power supply 44 also includes one or more capacitors. One or more capacitor banks 48 may be electrically coupled in parallel with the one or more capacitors provided in the power supply 44. As such, part of the power supplied to the laser 12 may be delivered by the one or more capacitors in the power supply 44 and a part of the power is delivered by the one or more capacitor banks 48. In some embodiments, the capacitor bank(s) 48 supply at least 75% of the required power to the laser 12.

The conversion of electricity from the AC mains 40 to the capacitors 50 may be about 70% efficient. The capacitors 50 typically charge when the laser 12 is not pulsing. In some embodiments, the capacitors 50 may charge continuously, and discharge during the ON duration of the pulses. In some instances, the capacitors are connected in parallel with the power supply 44, and draw charge unless there is a load across them (e.g., the laser 12 is being triggered) or they are fully charged. In some such instances, upon triggering of the laser 12, transistors in the power supply 44 create a load for the capacitors such that they discharge. After the capacitors discharge they may recharge again by drawing current from the power supply 44. Configuring the pulsing of the laser 12 at a low duty cycle may allow the capacitors 50 adequate time to recharge. In some embodiments, the laser 12 is configured to have a maximum average power level under 50% of the high peak laser power. Having the maximum average power level of the laser under 50% of the high peak laser power can increase the thermal compliance of the laser and may aid in efficient cooling thereof. The maximum average power level of the laser is generally specified by the laser manufacturer and is generally described as the highest possible average power output of the laser 12. For lasers that are CW operated, average laser power output is typically the same as the maximum average power level.

The laser 12 may be operated using one or more controllers 16. The controllers 16 may, for example, trigger or untrigger the laser 12. In some embodiments, the controllers 16 may determine a particular DC power level at which to trigger the laser or, in some cases, which capacitors to discharge upon triggering the laser (e.g., in an embodiment in which not all capacitors are discharged upon triggering). Pulsing the laser 12 can result in a lower average laser power. The laser system 10 may be pulsed at a low duty cycle in order to provide the lower average power level though the laser pulses have a high peak laser power.

Figure 4:
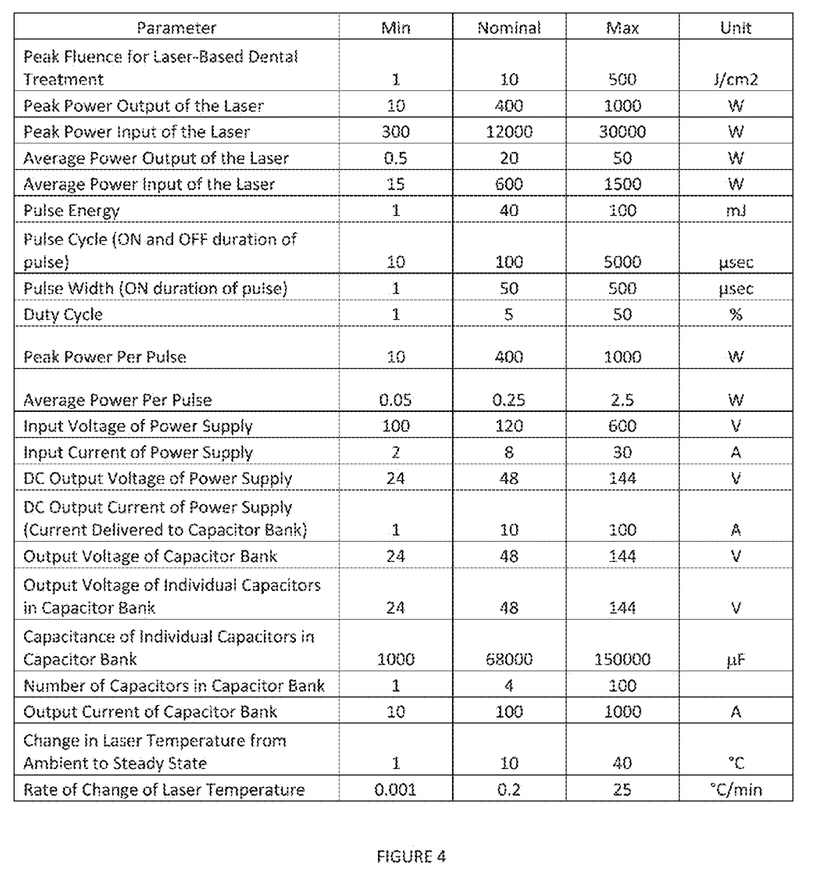
FIG. 4 is a chart showing example minimum, maximum, and nominal parameters of the laser system, according to various embodiments.

FIG. 4 is a chart showing example minimum, maximum, and nominal parameters of the laser system 10, according to various embodiments. In some embodiments, the laser 12 is operated at a lower average laser power that is 10% or less of peak laser power. In other embodiments, the lower average laser power is less than or equal to approximately 20%, 30%, 40%, 50%, 60%, 70%, 80%, or 90% of peak laser power. An average laser power greater than 60% of the peak laser power is avoided in some embodiments. In some instances, average power input of the laser may be, e.g., 15 W, 50 W, 75 W, 100 W, 200 W, 300 W, 400 W, 500 W, 600 W, 700 W, 1000 W, 1250 W, 1500 W, etc.; while average power output of the laser may be, e.g., 0.5 W, 1 W, 2 W, 5 W, 10 W, 20 W, 30 W, 40 W, 50 W, etc. In some instances, peak power input of the laser may be, e.g., 300 W, 400 W, 500 W, 1000 W, 2500 W, 5000 W, 7500 W, 10,000 W, 12,000 W, 15,000 W, 20,000 W, 25,000 W, 30,000 W, etc.; while peak power output of the laser may be, e.g., 10 W, 20 W, 50 W, 100 W, 200 W, 300 W, 400 W, 500 W, 750 W, 1000 W, etc. The above listed example values may also be exhibited for average power per pulse and peak power per pulse, in embodiments in which the laser 12 is a pulsed laser. If the laser 12 has a conversion efficiency of approximately 15% from electrical power to laser power, a peak electrical power required at the instant the laser 12 is pulsed may be at least 600 W, and may be as high as 1500 W, or even 2660 W.

The laser 12 may generate a beam having a wavelength of about 9.3 µm and a spot size focused to about 250 µm. With the spot size focused to about 250 µm and a peak laser power of below approximately 50 W, the low irradiance delivered may be insufficient to ablate hard dental tissue (e.g., tooth enamel). With the spot size focused to about 250 µm and a peak laser power of approximately 300 W a high irradiance can be delivered that may be sufficient to ablate hard dental tissue (e.g., tooth enamel). In some instances, the pulse energy delivered by the laser 12 may be, e.g., 1 mJ, 2 mJ, 3 mJ, 5 mJ, 10 mJ, 20 mJ, 30 mJ, 40 mJ, 50 mJ, 60 mJ, 70 mJ, 80 mJ, 90 mJ, 100 mJ, etc.

In some instances, the pulse width (e.g., ON duration of pulse) may be, e.g., 1 µs, 2 µs, 3 µs, 5 µs, 7 µs, 10 µs, 20 µs, 30 µs, 50 µs, 70 µs, 100 µs, 200 µs, 300 µs, 400 µs, 500 µs, etc. The pulse cycle/period (e.g., ON and OFF duration of pulse) may be, e.g., 10 µs, 20 µs, 30 µs, 50 µs, 100 µs, 200 µs, 300 µs, 500 µs, 1000 µs, 2000 µs, 3000 µs, 4000 µs, 5000 µs, etc. As a result, the duty cycle (defined herein as pulse width/pulse cycle) of the laser 12 may be, e.g., 1%, 2%, 5%, 7%, 10%, 20%, 30%, 50%, etc. Thus, in some instances, peak fluence delivered by the laser 12 may be, e.g., 1 J/cm$^2$, 2 J/cm$^2$, 3 J/cm$^2$, 5 J/cm$^2$, 7 J/cm$^2$, 10 J/cm$^2$, 20 J/cm$^2$, 30 J/cm$^2$, 50 J/cm$^2$, 100 J/cm$^2$, 200 J/cm$^2$, 300 J/cm$^2$, 400 J/cm$^2$, 500 J/cm$^2$, etc. Laser fluences as low as about 5 J/cm$^2$ can irreversibly affect the surface of hard dental tissue (e.g., enamel and dentin in teeth), at wavelengths in the range of 9.3 to 9.6 µm, at pulse durations on the order of 10 µs. Therefore, providing a laser beam at a wavelength in the range of about 9.3 to about 9.6 µm having a irradiance of 50,000 W/cm$^2$ may be sufficient to ablate hard dental tissue such as enamel. Various values described in FIG. 4 include a tolerance of 0.05%, 0.1%, 1%, 1.5%, 5%, 10%, 15%, 20%, etc.

As the laser may be pulsed at a low duty cycle, it is possible for one or more capacitors 50, having a large capacitance, to provide, at the instant the laser is pulsed, the peak electrical power required to provide laser pulses having a high peak laser power. The use of capacitors 50, having a large capacitance, allows for an AC to DC power supply 44 to be used that provides, over time, only the electrical power required for the laser to produce the lower average laser power and not the peak electrical power required by the laser during the instant the laser is pulsed. For example, if the peak electrical power required per laser pulse is 4 KW and the laser is operated with a low duty cycle of 3%, then the AC to DC power supply 44 need only be capable of providing electrical power of 120 W over time. Short-duration laser pulses of approximately 1 µs to 500 µs, from a laser system having an electrical power system capable of providing a peak electrical power of 4 KW instantaneously can, in some instances, ablate hard dental tissue (e.g., dentin, enamel, etc.). Those skilled in the art will appreciate that this electrical power system design is illustrative and that other selections, configurations, and grades of electrical power system components may be utilized to provide electrical power for a dental laser system 10 with high peak laser power and lower maximum average laser power. Such an electrical power system, used in combination with one or more capacitor banks, need not be rated to provide the electrical power needed to produce the peak output laser power and, instead, can be rated to provide the electrical power needed to produce the average output laser power.

In some embodiments, the laser 12 may be operated to produce a lower average laser power such that the amount of heat generated by the laser 12 is less than that produced using high peak power rated power supplies, which generally require removal of the heat using active refrigeration systems. As a result, in certain embodiments, a cooling system may be employed that can remove heat without needing refrigeration. The cooling system may include a radiator, a pump, a flow sensor, a level sensor, and a temperature switch. The radiator may be, for example, a Swiftech MCRx20-XP radiator that may incorporate dual 120 mm fans. The pump may be, for example, a Swiftech MCP655-B 12V pump provided by Swiftech of Long Beach, Calif. The flow sensor may be, for example, a Compac 5-20 series flow switch. The level sensor may be, for example, a Compac 10-782 level switch, and the temperature switch may be a Compac 11-800; all Compac components being obtained from Compac of Paradise, Calif.

In some embodiments, the user of the dental laser system 10 sets treatment parameters using the control 16; these parameters may typically include pulse duration, pulse repetition rate, and duty cycle, as well as treatment time and treatment pattern. The controller 16 may include a foot pedal or other manually controlled switch for turning the laser 12 on and off for treatment use. Laser parameters such as pulse power, pulse duration, duty cycle, pulse repetition rate, lower average laser power and high peak laser power can play a role in efficacy can effectiveness of the treatment, and may be adjusted using the foot pedal and/or another switch. In response to some parameters set by a user, the controller 16 can automatically determine additional parameters needed for effective and efficient treatment. To this end, the controller may use values of various parameters according to FIG. 4, and relations between such parameters, as described above.

In some embodiments, the laser 12 is configured to sink heat produced in the laser 12 during the production of laser pulses having a high peak laser power. Configuring the laser to have a large mass and thermal capacitance can increase the amount of heat that may be sunk/dissipated, thus limiting rise in the temperature of the laser. Typically, the greater the high peak laser power of a gas discharge laser, the greater the mass and the thermal capacitance of the laser. An example of a gas discharge laser configured with a suitable mass and thermal compliance is a Coherent E-150i from Coherent, Inc. of Bloomfield, Conn. Production of the laser pulses generally produces heat in the laser, which can increase the temperature of the laser. Sinking the heat in the laser can dampen the temperature increase resulting from production of laser pulses having a high peak laser power. Dampening of the temperature increase of the laser may allow for heat to be removed more slowly, e.g., using a cooling system configured to remove heat produced by the laser operating at the lower average laser power rather than at the high peak laser power.

In some instances, a gas discharge laser is between 5% and 20% efficient in converting electrical power to optical power. Therefore, a conventional laser operating at 15% efficiency and a high peak power of 300 W would typically require a cooling system configured to remove heat produced at the heat peak laser power, which may require a cooling capacity greater than 1700 W. In contrast, a laser system 12 configured as described herein, may only require a cooling system configured to remove heat produced at the lower average laser power of 10 W, e.g., having a cooling capacity or around 57 W, for example. In some embodiments, the laser system 10 is configured to maintain the lower average laser power such that the heat produced by the operation of the laser 12 is below a limit that would require heat removal with an active refrigeration unit. Active refrigeration requires providing a fluid having a temperature that is less than that of ambient air for cooling. As used herein, active refrigeration is understood to include chillers and refrigeration units, and may be undesirable due to complexity, cost and space required to accommodate the refrigeration components.

The laser system 10 described herein may be configured to produce a low average laser power. Thus, laser system 10 may be cooled through removal of heat to the ambient air. A cooling system configured to remove heat to the ambient air may employ a temperature differential between the ambient air and the cooling system to generate heat flow or transfer. The heat may be removed at a rate of heat transfer that is proportional to the temperature differential or a function thereof and a heat flow factor, such as a coefficient of convection. The rate of heat transfer may be increased by increasing the coefficient of convection.

Figure 5:
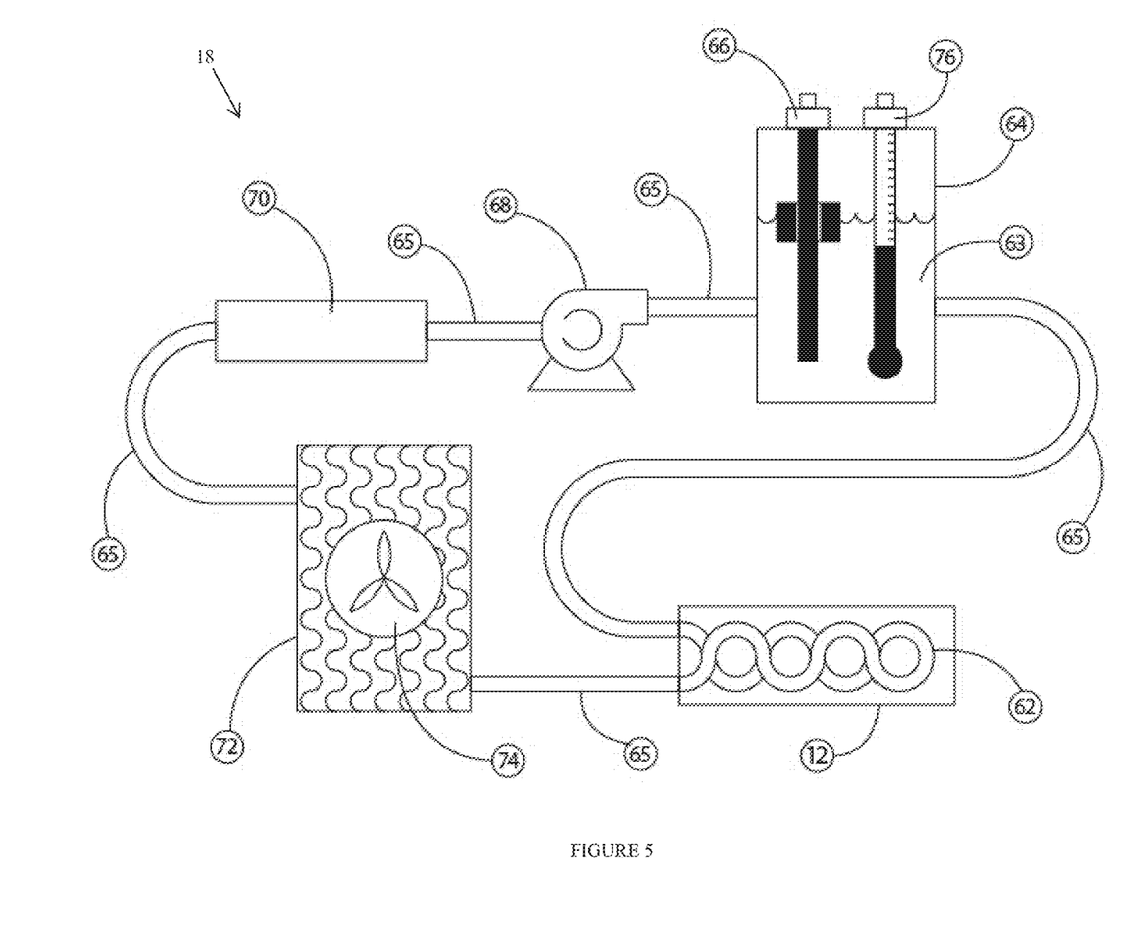
FIG. 5 is a block diagram of a laser cooling system, according to various embodiments.

An example of such a cooling system 18 is shown in greater detail in FIG. 5, which shows the laser 12 having a coolant path 62 that includes thermally conductive internal tubes and flow passages. The coolant path 62 allows the lower temperature coolant 63 to flow into the laser 12, absorb heat from the laser 12, and flow out at a higher temperature. The coolant 63 may include water which may include additives, e.g., algaecides, anti-freeze, fungicides, and corrosion inhibitors. The coolant 63 may be stored in a reservoir 64, wherein a level sensor 66 may activate an alarm or prevent operation of the laser 12 if coolant level falls to or below a specified minimum level. The cooling system 18 may also include a pump 68 for circulating the coolant 63, a flow sensor 70 for monitoring coolant flow, a radiator 72 to aid in transferring heat removed from the laser 12, a fan 74 for cooling the radiator 72, and a temperature sensor 76 for measuring the temperature of the coolant 63. Each of these components is optional. A shown, the components may be connected with tubing 65 which may be flexible, rigid or a mixture of both.

In some cases, the pump 68 may be run continuously, providing a flow of coolant 63 through the laser 12 whether or not the laser 12 is pulsing. The pump 68 and fan 74 may alternatively be configured to run as long as the coolant 63 is detected to be above a threshold temperature. The flow sensor 70 may activate an alarm and prevent laser function if coolant flow is not detected or detected to be at or below a specified threshold. The radiator 72 may have thermally conductive passageways for the coolant 63 which may include fins and/or other high surface area structures for highly efficient transfer of heat from the coolant 63 to the radiator 72, and then from the radiator 72 to the ambient air. The fan 74 can move air through and around the radiator 72 to aid in removal of heat. In some instances, the temperature sensor 76 may activate an alarm and prevent laser function if coolant temperature is at or above a specified threshold. The fan 74 may be configured to turn ON, increase or decrease speed, or turn OFF, to control the rate of air movement through and around the radiator 72 in response to coolant temperature. In some instances, the cooling system 18 may be configured not to permit a coolant 63 temperature of more than 20° C., 25° C., 30° C., 35° C., 40° C., 45° C., 50° C., etc. during operation, even during continuous operation. Should the coolant temperature reach or exceed a specified threshold, one or more parameters of the cooling system, such as fan speed may be adjusted, an alarm may be activated, and/or the laser operation may be stopped. In some instances, the laser may be operated at less than approximately 50% on-time.

FIG. 5 shows the cooling system 18 components in an exemplary orientation and flow order, but the ordering of the components may be changed and may still allow for adequate cooling. Those skilled in the art will appreciate that this cooling system design is illustrative and that other selections, configurations, and grades of cooling elements and components may be utilized to achieve a suitable non-refrigerated cooling system for a high peak power, low average power laser system.

Figure 6A:
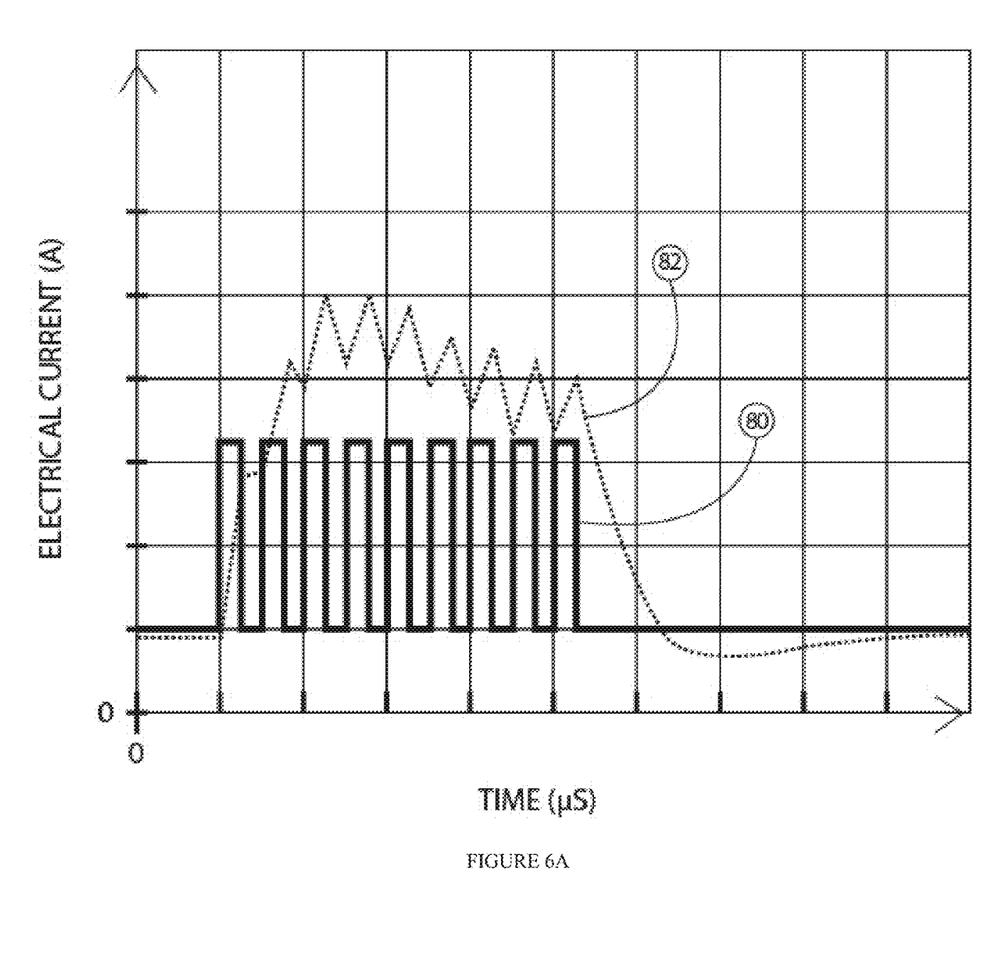
FIGS. 6A-6B are plots of example pulse trains for the laser system, according to various embodiments.

FIG. 6A shows an example pulse train that may be used in various embodiments described herein. FIG. 6A shows a burst of pulses that has nine pulses having pulse widths of about 40 µs and a repetition rate of about 10 KHz. In some cases, the burst may be repeated at a repetition rate of 124 Hz. A Coherent E-150i laser operating at these parameters may exhibit a lower average laser power that ranges from 19 W to 21 W and a high peak laser power of about 450 W. FIG. 6A shows an example laser trigger signal 80. The laser trigger signal may be a TTL signal that is provided by the controller 16 to operate the laser. An example peak current signal 82 (e.g., the electrical current being drawn by the laser) is also shown in FIG. 6A. It can be seen from FIG. 6A that the peak current may be at its greatest during pulsed operation of the laser. With a required voltage of 48 VDC, for example, the peak electrical power of the laser is equal to the peak current times the required voltage, or in this example about 1900 W, which is the maximum peak power of the laser in one embodiment.

Figure 6B:
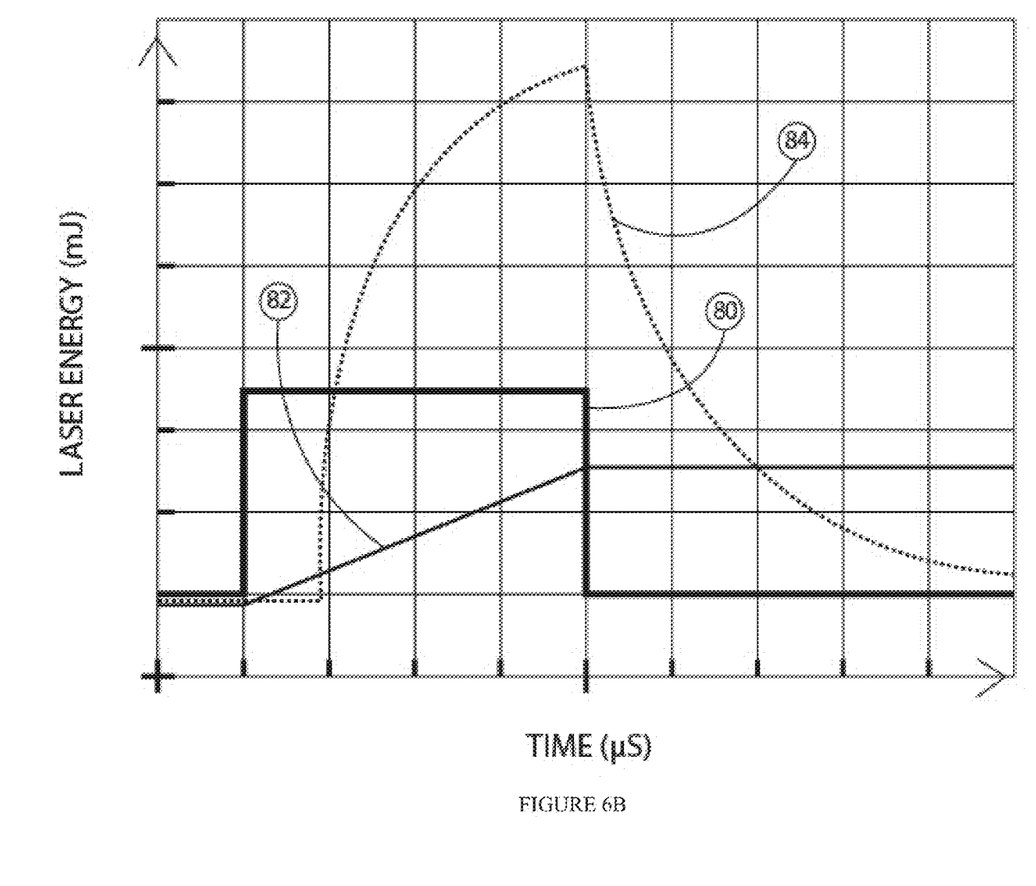

FIG. 6B shows an example laser pulse 84 having an optical energy measured in mJ. The laser trigger signal 80 has a pulse width of 40 µs and the laser pulse 84 is offset by about 8 µs relative to the trigger signal 80. In this example, it can be seen that the laser pulse has a time profile that resembles the shape of a shark fin as the optical energy rises and falls according to exponential decay functions. The integrated total optical energy delivered by the laser pulse shown in FIG. 6B is about 18 mJ. A pulse width of 40 μs of the laser pulses yields a high peak output laser power of about 450 W.

Figure 7:
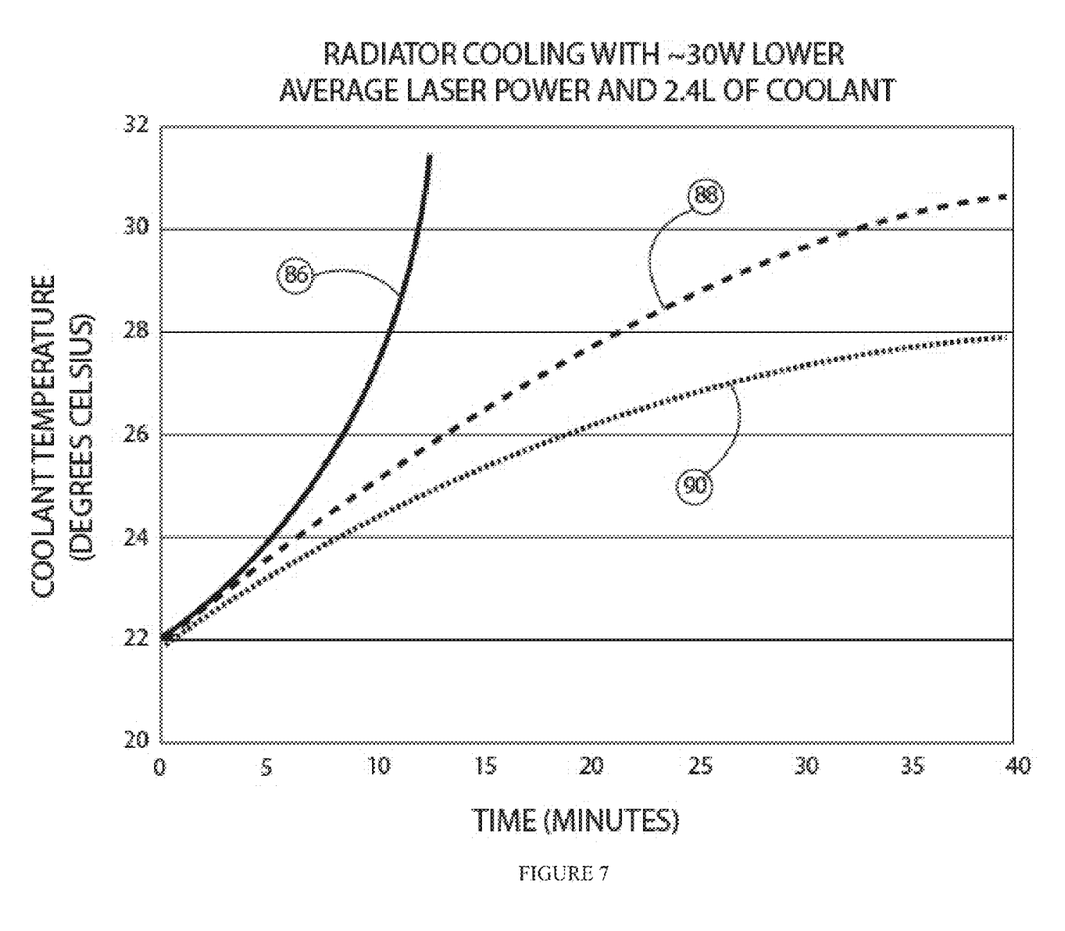
FIG. 7 is an example plot of coolant temperature vs. time, according to various embodiments.

FIG. 7 shows an example plot of coolant temperature vs. time for 2.4 L of coolant being used in conjunction with a Swiftech MCRx20-XP radiator to cool an example laser 12 shown in FIG. 1. The example laser 12 is operated with about 10% efficiency and at a lower average laser power of about 30 W. A 0-fan temperature curve 86 shows the temperature of the coolant when cooling is performed without a fan. It can be seen that the 0-fan temperature curve 86 has a shape of an exponential growth function. A single-fan temperature curve 88 shows the temperature of the coolant when cooling is performed with a single fan. It can be seen that the coolant temperature eventually exceeds 30° C. with the single fan (e.g., around the 30 minute mark). A dual-fan temperature curve 90 shows the temperature of the coolant when cooling is performed with dual fans. It can be seen that the coolant temperature approaches an asymptote below 30° C. with the dual fans. Therefore, the dual fans in these circumstances can prevent the laser from overheating.

The example system described with reference to FIG. 7 illustrates that a laser operating relatively inefficiently at 10% and having a relatively large lower average laser power of about 30 W may be cooled by removing the heat to ambient air, and does not require active an refrigeration system in order to maintain the coolant temperature below 30° C. The Coherent E-150i laser may automatically prevent operation when the coolant temperature is at or above a specified temperature (e.g., 35° C.). Operating the laser with coolant below a particular temperature (e.g., 30° C.) can allow the Coherent E-150i laser to operate without overheating.

Figure 8:
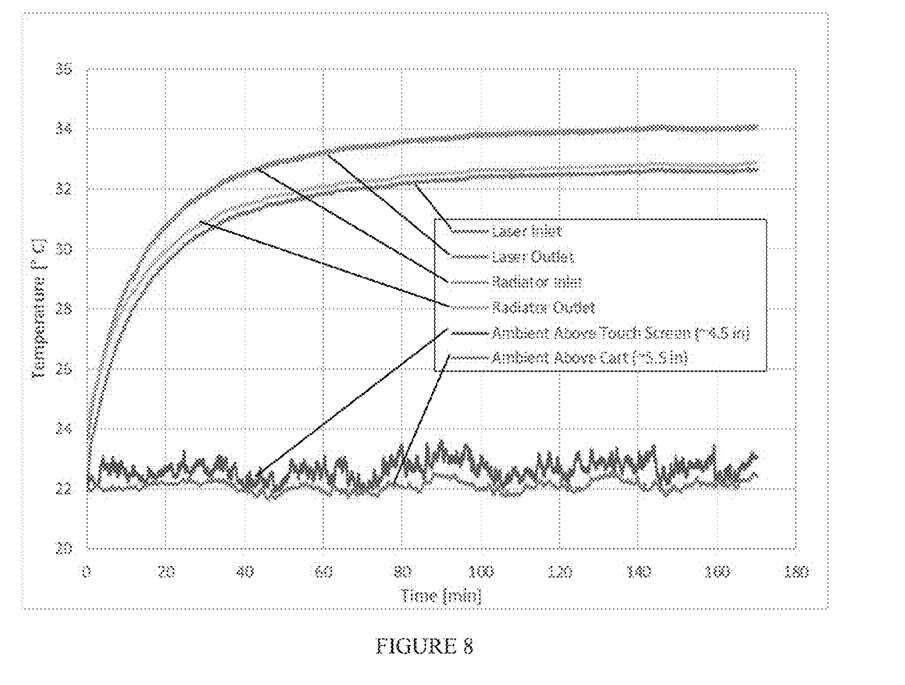
FIG. 8 is an example plot of temperature at various locations of the laser system vs. time, according to various embodiments.

In many conventional lasers, active refrigeration is used to cool gas discharge lasers of this size. This is because active refrigeration systems typically maintain a substantially constant coolant temperature, and the laser can operate more consistently when the temperature is maintained at a substantially constant level. However, such systems add size, cost, and complexity to the laser system. A cooling system that can remove heat to the ambient air and allows the coolant and also the laser to vary in temperature within a specified limit, as described in certain embodiments herein, allows for a smaller, simpler, cheaper design, while still preventing the laser from overheating. FIG. 8 shows an example plot of temperature vs. time at various locations of the laser system 10 and cooling system 18, according to some embodiments. In various embodiments, the laser 12 may exhibit a change in temperature from an ambient state (e.g., at room temperature, e.g., 20-22° C.) to a steady state (e.g., fully operating) of, e.g., 1° C., 2° C., 5° C., 10° C., 15° C., 20° C., 25° C., 30° C., 35° C., 40° C., etc.

One advantage of operating a laser with a high peak laser power at a lower maximum average laser power is that, in some embodiments, the magnitude of temperature rise as a result of heat may be reduced, and the rate of temperature rise may be slowed. In various embodiments, the rate of change of the temperature of the laser 12 may be, e.g., 0.001° C./min, 0.01° C./min, 0.1° C./min, 0.2° C./min, 0.5° C./min, 1° C./min, 2° C./min, 5° C./min, 10° C./min, 25° C./min, etc. Thus, a laser with a high peak laser power at a lower maximum average laser power may have less temperature variability. A number of laser functions and variables, such as pointing, delivery of optical power, and beam shape and divergence, may depend on the laser temperature. Reducing temperature variability of the laser system can mitigate the effects of temperature variations on such temperature-dependent laser functions. Other advantages to using a laser of this type are explained in U.S. Pat. No. 8,251,984, which, as stated earlier, is incorporated herein by reference in its entirety.

Some embodiments of the system described herein include a cooling system that includes fans that blow ambient air over the laser 12, thereby cooling the laser without the need for coolant. Some embodiments of the cooling system include the level sensor 66 connected to a valve and water supply, such that if the coolant level in the reservoir 64 falls to a threshold low level, the level sensor 66 can actuate the valve until the coolant level is sufficiently high and may then turn off the valve.

The terms and expressions employed herein are used as terms and expressions of description and not of limitation, and there is no intention, in the use of such terms and expressions, of excluding any equivalents of the features shown and described or portions thereof. In addition, having described certain embodiments of the invention, it will be apparent to those of ordinary skill in the art that other embodiments incorporating the concepts disclosed herein may be used without departing from the spirit and scope of the invention. The structural features and operational functions of the various embodiments may be arranged in various combinations and permutations, and all are considered to be within the scope of the disclosed invention. Accordingly, the described embodiments are to be considered in all respects as only illustrative and not restrictive. Furthermore, the configurations, materials, and dimensions described herein are intended as illustrative and in no way limiting. Similarly, although physical explanations have been provided for explanatory purposes, there is no intent to be bound by any particular theory or mechanism, or to limit the claims in accordance therewith.

What is claimed is:

1. A laser system comprising:
   a laser for generating a pulsed laser beam;
   a controller configured to trigger the laser at a specified peak output laser power and at an average output laser power of less than approximately 50% of the specified peak output laser power;
   a power source supplying input laser power to the laser and rated at less than input laser power corresponding to the specified peak output laser power; and
   a capacitor bank comprising at least one capacitor and configured for charging the at least one capacitor from the power source and for delivering to the laser at least a portion of an input laser power corresponding to the specified peak output laser power during an ON duration of a pulse.

2. The laser system of claim 1, wherein a wavelength of the laser is in a range from 8 μm up to 12 μm.

3. The laser system of claim 1, wherein the laser comprises a laser rated to have a maximum average output laser power level less than approximately 50% of the specified peak output laser power.

4. The system of claim 1, wherein the specified peak output laser power is within a range from 10 W up to 1,000 W.

5. The system of claim 1, wherein the controller is adapted to adjust the average output laser power within a range from 0.5 W up to 50 W.

6. The system of claim 1, wherein the controller is adapted to adjust the average output laser power within a range from 0.5 W up to 500 W.

7. The system of claim 1, wherein the controller is adapted to adjust the average output laser power to a level of at least 50 W.

8. The system of claim 1, wherein the controller is adapted to limit the average output laser power up to 10% of the specified peak output laser power.

9. The system of claim 1, wherein the controller is adapted to limit the average output laser power up to 5% of the specified peak output laser power.

10. The system of claim 1, wherein the controller is adapted to adjust a duration of the pulse of the pulsed laser beam within a range from 10 is up to 5,000 µs.

11. The system of claim 1, wherein the controller is adapted to adjust a duty cycle of the pulse of the pulsed laser beam within a range from 1% up to 50%.

12. The system of claim 1, wherein:
an output voltage of the capacitor bank is within a range from 24 V up to 144 V; and
a peak output current of the capacitor bank is within a range from 10 A up to 1,000 A.

13. The system of claim 1, wherein a number of capacitors in the capacitor bank is in a range from 1 up to 100.

14. The system of claim 1, wherein a capacitance of a first capacitor in the capacitor bank is within a range from 1,000 µF up to 150,000 µF.

15. The system of claim 1, wherein the controller is adapted to adjust the peak output laser power to a level sufficient to ablate dental enamel.

16. The system of claim 1, wherein the controller is adapted to operate the laser at an average output laser power less than a rated maximum average output laser power level of the laser.

17. The system of claim 1, wherein the laser comprises a waveguide in at least one optical resonator axis.

18. The system of claim 1, wherein the laser comprises a gas discharge laser.

19. The system of claim 18, wherein the gas discharge laser comprises a $CO_2$ laser.

20. The system of claim 1, further comprising a non-refrigerant-based cooling system for controlling an operating temperature of at least the laser.

21. The system of claim 20, wherein the cooling system comprises:
at least one laser coolant path in thermally conductive communication with the laser;
a coolant reservoir for containing a coolant;
a pump for circulating the coolant; and
a radiator having at least one heat-conducting pathway therethrough.

22. The system of claim 21, wherein the cooling system further comprises at least one of:
a level sensor for measuring a level of the coolant in the coolant reservoir;
a temperature sensor for measuring temperature of the coolant;
a flow sensor for measuring flow of the coolant; and
a fan directing air flow to the heat-conducting pathway.

23. The system of claim 22, wherein the controller is adapted to suspend operation of the laser based on an output from at least one of the level sensor, the temperature sensor, and the flow sensor.

24. The system of claim 22, wherein the controller is adapted, based on an output from the temperature sensor, to at least one of:
adjust the pump to adjust a flow of the coolant; and
operate the fan.

25. The system of claim 24, wherein the controller is adapted to at least one of adjust the pump and operate the fan so as to limit a temperature of the coolant to at most 30° C.

26. The system of claim 21, wherein the coolant comprises water.

27. The system of claim 1, wherein the portion of the input laser power comprises at least 75 percent of the input laser power.

28. A method of operating a laser, the method comprising the steps of:
generating a pulsed laser beam, generation of laser pulses comprising configuring the laser to trigger at a specified peak output laser power and at an average output laser power of less than approximately 50% of the specified peak output laser power;
charging at least one capacitor in a capacitor bank using a power source rated at less than an input laser power corresponding to the specified peak output laser power; and
delivering to the laser from the capacitor bank at least a portion of the input laser power corresponding to the specified peak output laser power during an ON duration of a laser pulse.

29. The method of claim 28, wherein a wavelength of the laser is in a range from 8 µm up to 12 µm.

30. The method of claim 28, wherein the laser comprises a laser rated to have a maximum average output laser power level less than approximately 50% of the specified peak output laser power.

31. The method of claim 1, wherein the specified peak output laser power is within a range from 10 W up to 1,000 W.

32. The method of claim 1, wherein the configuring step further comprises adjusting the average output laser power within a range from 0.5 W up to 50 W.

33. The method of claim 1, wherein the configuring step further comprises adjusting the average output laser power within a range from 0.5 W up to 500 W.

34. The method of claim 1, wherein the configuring step further comprises adjusting the average output laser power to a level of at least 50 W.

35. The method of claim 1, wherein the configuring step further comprises limiting the average output laser power up to 10% of the specified peak output laser power.

36. The method of claim 1, wherein the configuring step further comprises limiting the average output laser power up to 5% of the specified peak output laser power.

37. The method of claim 1, wherein the configuring step further comprises adjusting a duration of the pulse of the pulsed laser beam within a range from 10 µs up to 5,000 µs.

38. The method of claim 1, wherein the configuring step further comprises adjusting a duty cycle of the pulse of the pulsed laser beam within a range from 1% up to 50%.

39. The method of claim 1, wherein the delivering step comprises:
delivering an output voltage within a range from 24 V up to 144 V; and
delivering a peak output current within a range from 10A up to 1,000A.

40. The method of claim 1, wherein a number of capacitors in the capacitor bank is in a range from 1 up to 100.

41. The method of claim 1, wherein a capacitance of a first capacitor in the capacitor bank is within a range from 1,000 µF up to 150,000 µF.

42. The method of claim 1, wherein the configuring step further comprises adjusting the peak output laser power to a level sufficient to ablate dental enamel.

43. The method of claim 1, wherein the configuring step further comprises configuring the laser to operate at an average output laser power less than a rated maximum average output laser power level of the laser.

44. The method of claim 1, further comprising:
controlling an operating temperature of at least the laser using a non-refrigerant-based cooling system.

45. The method of claim 44, further comprising:
obtaining an output from at least one of a level sensor, a temperature sensor, and a flow sensor of the non-refrigerant-based cooling system; and
suspending operation of the laser based on the reading.

46. The method of claim 44, further comprising
obtaining an output from a temperature sensor of the non-refrigerant-based cooling system; and
at least one of: (i) adjusting a flow of coolant and (ii) operating a fan, based on the reading.

47. The method of claim 46, wherein at least one of (i) adjusting the flow and (ii) operating the fan limits a temperature of the coolant to at most 30° C.

* * * * *

UNITED STATES PATENT AND TRADEMARK OFFICE
CERTIFICATE OF CORRECTION

PATENT NO. : 9,450,369 B2
APPLICATION NO. : 14/952396
DATED : September 20, 2016
INVENTOR(S) : Nathan P. Monty et al.

It is certified that error appears in the above-identified patent and that said Letters Patent is hereby corrected as shown below:

In claim 10, column 15, line 13, replace "is" with -- µs --.

Signed and Sealed this
Twentieth Day of December, 2016

Michelle K. Lee
*Director of the United States Patent and Trademark Office*